(12) United States Patent
Micheyl et al.

(10) Patent No.: US 10,537,268 B2
(45) Date of Patent: *Jan. 21, 2020

(54) AUTOMATED ASSESSMENT AND ADJUSTMENT OF TINNITUS-MASKER IMPACT ON SPEECH INTELLIGIBILITY DURING USE

(71) Applicant: Starkey Laboratories, Inc., Eden Prairie, MN (US)

(72) Inventors: Christophe D. Micheyl, Saint Genis Laval (FR); Sridhar Kalluri, El Cerrito, CA (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 248 days.

This patent is subject to a terminal disclaimer.

(21) Appl. No.: 15/654,205

(22) Filed: Jul. 19, 2017

(65) Prior Publication Data

US 2018/0279922 A1    Oct. 4, 2018

Related U.S. Application Data

(63) Continuation-in-part of application No. 15/475,965, filed on Mar. 31, 2017, now Pat. No. 10,405,112.

(51) Int. Cl.
| | | |
|---|---|---|
| *H04R 25/00* | (2006.01) | |
| *A61B 5/12* | (2006.01) | |
| *G10L 13/00* | (2006.01) | |

(52) U.S. Cl.
CPC .............. *A61B 5/121* (2013.01); *H04R 25/50* (2013.01); *G10L 13/00* (2013.01); *H04R 25/505* (2013.01)

(58) Field of Classification Search
CPC ........ A61B 5/121; A61B 5/128; H04R 25/50; H04R 25/75
(Continued)

(56) References Cited

U.S. PATENT DOCUMENTS

| | | |
|---|---|---|
| 5,403,262 A | 4/1995 | Gooch |
| 5,729,658 A | 3/1998 | Hou et al. |

(Continued)

FOREIGN PATENT DOCUMENTS

| | | |
|---|---|---|
| DE | 102011001793 | 10/2012 |
| WO | WO-96000051 A1 | 1/1996 |
| WO | WO-2008106975 A2 | 9/2008 |

OTHER PUBLICATIONS

"U.S. Appl. No. 15/475,965, Non Final Office Action dated Jun. 26, 2018", 12 pgs.

(Continued)

*Primary Examiner* — John P Lacyk
(74) *Attorney, Agent, or Firm* — Schwegman Lundberg & Woessner, P.A.

(57) ABSTRACT

Disclosed herein, among other things, are apparatus and methods for automated assessment and adjustment of tinnitus-masker impact on speech intelligibility during use of the tinnitus-masker. In various embodiments, a method of fitting a tinnitus-masker device for a patient is provided. The method includes using a speech intelligibility model to predict impact of therapy provided by the tinnitus-maker device on speech understanding of the patient. A parameter of the tinnitus-masker device is automatically adjusted during use to reduce the impact of the therapy provided by the tinnitus-maker device on speech understanding of the patient, according to various embodiments.

20 Claims, 6 Drawing Sheets

(58) Field of Classification Search
USPC .......................................................... 600/25
See application file for complete search history.

(56) References Cited

U.S. PATENT DOCUMENTS

| | | |
|---|---|---|
| 7,650,005 B2 | 1/2010 | Chalupper |
| 8,801,592 B2 | 8/2014 | Jensen et al. |
| 9,025,800 B2 | 5/2015 | Kidmose et al. |
| 9,525,950 B2 | 12/2016 | Andersen et al. |
| 9,900,712 B2 | 2/2018 | Galster |
| 9,913,053 B2 | 3/2018 | Jensen et al. |
| 10,405,112 B2 | 9/2019 | Micheyl et al. |
| 2001/0051776 A1 | 12/2001 | Lenhardt |
| 2005/0069162 A1 | 3/2005 | Haykin et al. |
| 2006/0245610 A1 | 11/2006 | Chalupper |
| 2011/0137111 A1 | 6/2011 | Hanley et al. |
| 2013/0039517 A1 | 2/2013 | Nielsen et al. |
| 2016/0080876 A1 | 3/2016 | Lunner |
| 2016/0094923 A1 | 3/2016 | Jensen et al. |
| 2016/0337769 A1 | 11/2016 | Siddhartha et al. |
| 2018/0007479 A1 | 1/2018 | Dundas |
| 2018/0288540 A1 | 10/2018 | Micheyl et al. |

OTHER PUBLICATIONS

Paglialonga, "Influence of Tinnitus Sound Therapy Signals on the Intelligibility of Speech", The Journal of Laryngology and Otology, 125(8), (Jun. 10, 2011), 795-801.

"U.S. Appl. No. 15/475,965, Final Office Action dated Jan. 10, 2019", 11 pgs.

"U.S. Appl. No. 15/475,965, Response filed Sep. 20, 2018 to Non Final Office Action dated Jun. 26, 2018", 7 pgs.

Mehraei, Golbarg, et al., "Spectrotemporal modulation sensitivity for hearing-impaired listeners: Dependence on carrier center frequency and the relationship to speech intelligibility", J. Acoust. Soc. Am. 136 (1), (Jul. 2014), 301-316.

Paglialonga, A, et al., "Influence of tinnitus sound therapy signals on the", The Journal of Laryngology & Otology, 125, (Jun. 10, 2011), 795-801.

Spitzer, J. B., et al., "Effect of tinnitus masker noise on speech discrimination in quiet and two noise backgrounds", Scand Audiol. 12(3), (1983), 197-200.

Woods, William S., et al., "Predicting the effect of hearing loss and audibility on amplified", J. Acoust. Soc. Am. 133 (6), (Apr. 11, 2013), 4268-4278.

"European Application Serial No. 18165145.6, Extended European Search Report dated Aug. 14, 2018", 10 pgs.

"U.S. Appl. No. 15/475,965, Preliminary Amendment filed Jun. 26, 2017", 7 pgs.

"U.S. Appl. No. 15/475,965, Supplemental Preliminary Amendment filed Aug. 21, 2017", 3 pgs.

"U.S. Appl. No. 15/475,965, Response filed Mar. 11, 2019 to Final Office Action dated Jan. 10, 2019", 7 pgs.

"U.S. Appl. No. 15/475,965, Notice of Allowance dated Apr. 17, 2019", 8 pgs.

"U.S. Appl. No. 15/475,965, Corrected Notice of Allowability dated Jul. 12, 2019", 2 pgs.

LEVELS OF MASKING AND SPEECH AT SELECT FREQUENCIES

| FREQUENCY (Hz) | 500 | 1000 | 2000 |
|---|---|---|---|
| TINNITUS STIMULUS LEVEL (dB SPL) | 34.0 | 32.5 | 32.3 |
| NORMAL SPEECH LEVEL (dB SPL) | 38.4 | 39.3 | 42.6 |
| DIFFERENCE (dB) | -4.4 | -6.8 | -10.3 |

Fig. 3

AUTOMATED ASSESSMENT AND ADJUSTMENT OF TINNITUS-MASKER IMPACT ON SPEECH INTELLIGIBILITY DURING USE

CROSS REFERENCE TO RELATED APPLICATIONS

This application is a continuation-in-part of U.S. patent application Ser. No. 15/475,965, entitled "AUTOMATED ASSESSMENT AND ADJUSTMENT OF TINNITUS-MASKER IMPACT ON SPEECH INTELLIGIBILITY DURING FITTING", filed on Mar. 31, 2017, which is hereby incorporated by reference herein in its entirety.

TECHNICAL FIELD

This document relates generally to hearing assistance systems and more particularly to automated assessment and adjustment of tinnitus-masker impact on speech intelligibility during use.

BACKGROUND

Hearing assistance devices, such as hearing aids, are used to assist patients suffering hearing loss by transmitting amplified sounds to ear canals. In one example, a hearing aid is worn in and/or around a patient's ear.

Tinnitus is a condition in which a patient perceives sound in their ear in the absence of corresponding external sound. While ringing of the ears is associated with tinnitus, other types of sounds can be perceived and can be sporadic, intermittent or continuous. Tinnitus can be caused by a number of conditions or injuries, but regardless of cause can be debilitating and decrease a patient's quality of life. A tinnitus-masker is a function of a hearing assistance device that can be used to provide therapy to a patient suffering from tinnitus.

There is a need in the art for improved mitigation of tinnitus-masker impact on speech intelligibility.

SUMMARY

Disclosed herein, among other things, are apparatus and methods for automated assessment and adjustment of tinnitus-masker impact on speech intelligibility during use. In various embodiments, a method of fitting a tinnitus-masker device for a patient is provided. The method includes using a speech intelligibility model to predict impact of therapy provided by the tinnitus-maker device on speech understanding of the patient. A parameter of the tinnitus-masker device is automatically adjusted during use to reduce the impact of the therapy provided by the tinnitus-maker device on speech understanding of the patient, according to various embodiments.

Various aspects of the present subject matter include a tinnitus masking hearing device for a patient. The device includes a sound generator configured to provide tinnitus masking therapy, and a processor connected to the sound generator. In various embodiments, the processor is programmed with instructions to perform a method of using the tinnitus masking hearing device. A speech intelligibility model is used to compute a first speech intelligibility score for speech without a tinnitus masking therapy provided by the tinnitus masking hearing device. The speech intelligibility model is used to compute a second speech intelligibility score for speech with the tinnitus masking therapy provided by the tinnitus masking hearing device. A difference is computed between the first speech intelligibility score and the second speech intelligibility score. If the difference exceeds a programmable threshold, a parameter of the tinnitus-masker device is adjusted to reduce the impact of the therapy provided by the tinnitus-maker device on speech understanding of the patient, in various embodiments.

Various aspects of the present subject matter include a non-transitory computer-readable storage medium that stores instructions for execution by processing circuitry of a tinnitus masking hearing device for a patient. The operations include using a speech intelligibility model to compute a first speech intelligibility score for speech without a tinnitus masking therapy provided by the tinnitus masking hearing device, and using the speech intelligibility model to compute a second speech intelligibility score for speech with the tinnitus masking therapy provided by the tinnitus masking hearing device. The operations further include computing a difference between the first speech intelligibility score and the second speech intelligibility score, and, if the difference exceeds a programmable threshold, adjusting a parameter of the tinnitus-masker device to reduce the impact of the therapy provided by the tinnitus-maker device on speech understanding of the patient, in various embodiments This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 3 illustrates a table showing levels of tinnitus masking and speech at select frequencies, according to various embodiments of the present subject matter.

DETAILED DESCRIPTION

Figure 1:
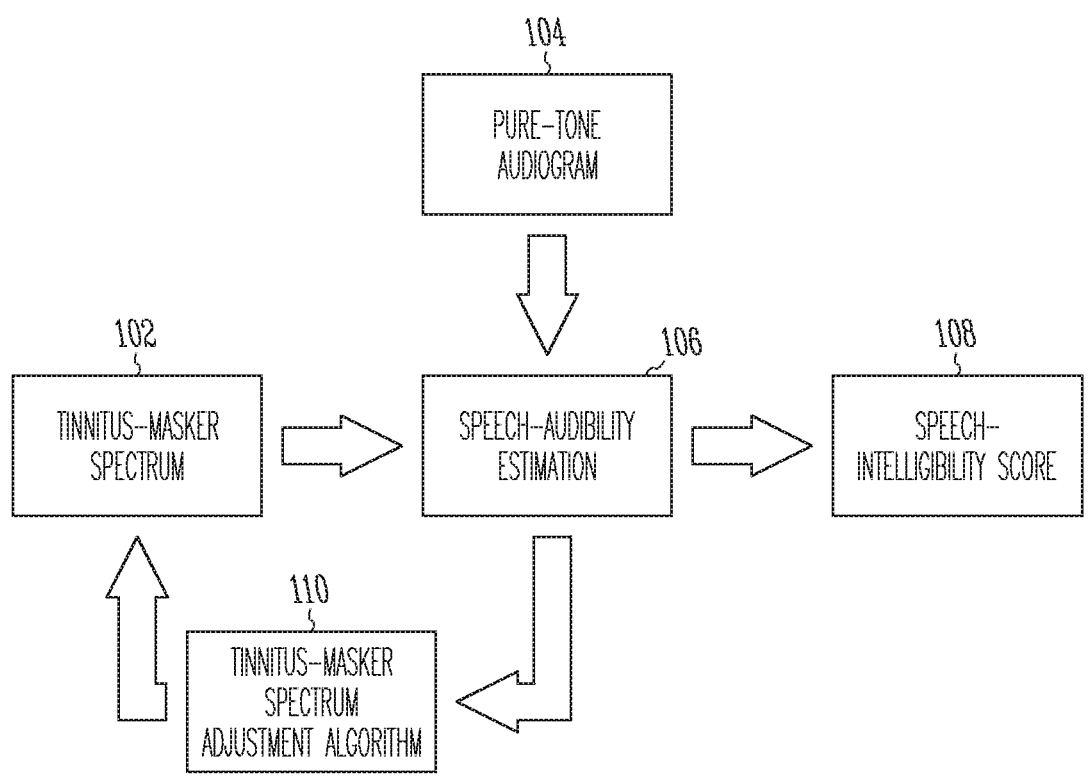
FIG. 1 illustrates a block diagram of a system for limiting tinnitus-masker impact on speech intelligibility, according to various embodiments of the present subject matter.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present detailed description will discuss hearing assistance devices using the example of hearing aids with tinnitus-maskers. Other hearing assistance devices include, but are not limited to, those in this document. It is understood that their use in the description is intended to demonstrate the present subject matter, but not in a limited or exclusive or exhaustive sense.

Tinnitus is a condition in which a patient perceives sound in their ear in the absence of corresponding external sound. While ringing of the ears is associated with tinnitus, other types of sounds can be perceived and can be sporadic, intermittent or continuous. Tinnitus can be caused by a number of conditions or injuries, but regardless of cause can be debilitating and decrease a patient's quality of life.

A common clinical solution for tinnitus involves listening to a continuous sound, aka 'tinnitus-masker', generated by a hearing aid or by some other device. The overall volume and in some cases the spectral shape of the masker are adjusted individually based on the patient's audiometric characteristics and/or listening preferences. In selecting these parameters, an important consideration is that the tinnitus masker does not interfere with the perception of external sounds of interest, such as speech. The present subject matter facilitates the selection of a tinnitus-masker that does not interfere substantially with the perception of speech. In various embodiments, this is achieved by using a speech-intelligibility model to automatically compute speech-intelligibility scores for different candidate tinnitus-maskers, and automatically adjusting the masker overall level and/or spectrum to keep the speech-masking effect under some pre-defined level.

Adjustment During Fitting

Wearers of hearing assistance devices undergo a process called "fitting" to adjust the hearing assistance device to their particular hearing and use. In such fitting sessions a wearer may select one setting over another. Other types of selections include changes in level, which can be a preferred level. Hearing assistance device settings may be optimized for a wearer through a process of patient interview and device adjustment.

Currently, clinicians who wish to offer their patients a tinnitus-masker adjust parameters of the masker during fitting such that they are adapted to the individual. Minimally, the clinician adjusts the overall level, or volume, of the masker, so that the masker is neither too faint, having no effect on tinnitus, or too loud to cause too much masking of relevant external sounds (such as speech). Clinicians may also adjust the spectrum, or level per frequency-band, of the masker, and possibly other parameters such as the modulation rate. In fitting a tinnitus masker, an important consideration is that the selected masker does not interfere with speech intelligibility. Previous tinnitus-masker generation systems do not include a mechanism for checking that the selected masker will not interfere with speech understanding. The present subject matter includes a speech-intelligibility prediction stage in tinnitus-masker fitting software, and uses the results of this modeling stage for automatically adjusting the overall level and/or spectrum of the tinnitus masker, so as to limit disruptions of speech understanding to a pre-defined level.

In various embodiments, the present subject matter uses a model of speech intelligibility (e.g., the speech-intelligibility index, or 'SII'), modified to account for hearing loss, to compute a speech-intelligibility score for normal or conversational-level speech with, and without, a tinnitus-masker. The difference between these two scores is computed, and it is used to determine whether the tinnitus masker is acceptable, or whether it is likely to disrupt speech intelligibility by more than a pre-defined acceptable amount, in various embodiments.

In one embodiment, if the tinnitus-masker's impact on speech intelligibility is acceptably small, nothing is done. However, if the tinnitus-masker's impact on speech intelligibility is too large to be accepted, an option is offered to the clinician to automatically adjust the overall level or spectrum or other parameter of the tinnitus masker, so as to limit the impact of the tinnitus-masker on speech intelligibility to an acceptable level, in various embodiments. In further embodiments, the option could be offered to the patient, if the tinnitus-masker fitting is performed by the patient him or herself. The adjustment of tinnitus masking parameters is done automatically, in various embodiments.

FIG. 1 illustrates a block diagram of system for limiting tinnitus-masker impact on speech intelligibility, according to various embodiments of the present subject matter. In various embodiments, the tinnitus-masker spectrum 102 as defined by the clinician or the patient is used as input, along with the patient's audiogram 104, to a speech-audibility estimation model 106. Based on the results, speech-intelligibility scores 108 are computed for normal conversational (approximately 65 to 70 dB SPL) speech with, and without, the tinnitus masker. If the speech-intelligibility score 108, or the speech audibility, with the masker is too low taking into account the speech-intelligibility score without the masker, an option is offered 110 to automatically adjust the masker spectrum to limit the impact on speech intelligibility, in various embodiments.

In various embodiments, the spectrum of the proposed tinnitus masker (M[f]) and pure-tone audiogram (T[f]) of the patient are input into a speech-intelligibility model to estimate the audibility (A[f]) of a normal conversational (65 to 70 dB SPL) speech signal (S[f]) in different frequency bands (denoted by the index, f) with the tinnitus masker (Am[f]) and without the tinnitus masker (An[f]). The computed audibility data are used to compute a global speech-intelligibility score (SI) with the masker (SIm) and without the masker (SIn). These two scores are used to compute a "corrected" score (SIc), as follows: SIc=SIm+g((1−SIn)*a), where a is a correction factor and g is a nonlinear transformation function (e.g., a scaled sigmoid function), in various embodiments.

According to various embodiments, if the corrected score (SIc) is lower than a predefined threshold (SIcrit), an option is offered to the user for automatically adjusting the proposed tinnitus spectrum, so as to limit the impact of the tinnitus masker on speech intelligibility. Formally, the adjusted tinnitus spectrum (Ma[f]) is computed as:

$$Ma[f]=M[f]-M[f]*h(1-z(Am[f],An[f],f))$$

where h and z are two non-linear functions. While the details of these two functions may vary, generally the level of the tinnitus masker is reduced in a frequency-dependent manner, so that masker levels tend to be more attenuated for frequency bands that contribute more to reducing speech audibility/intelligibility than for frequency bands that contribute less to reducing speech audibility/intelligibility. Moreover, the function, z, includes a regularization term, whereby attenuations applied to adjacent frequency bands are coupled, or smoothed to avoid large differences in the attenuations applied across adjacent frequency bands, which could create undesirable artifacts related to the presence of sharp spectral edges between adjacent bands.

In various embodiments, the computation of the predicted speech-intelligibility score contains a so-called proficiency factor. This variable influences the shape of the relationship between the computed audibility of the speech signal and the predicted speech intelligibility. The selection of the proficiency factor can be advantageously informed by the results of perceptual and/or cognitive tests, resulting in improved predictions of speech-intelligibility scores for different types of speech materials in hearing-impaired listeners—compared to predictions obtained without taking into account such additional information. For example, thresholds for the detection and/or discrimination of spectral, temporal, or spectro-temporal modulation, or the measured completion time for a Trail-making B test obtained in a listener could be used to estimate the proficiency factor for that listener.

Definition of Variables f: frequency-band index
M[f]: level per band (dB SPL) of the proposed tinnitus masker
S[f]: average level per band (dB SPL) of a normal (65 to 70 dB SPL) speech signal
T[f]: pure-tone threshold (dB SPL)

Figure 2:
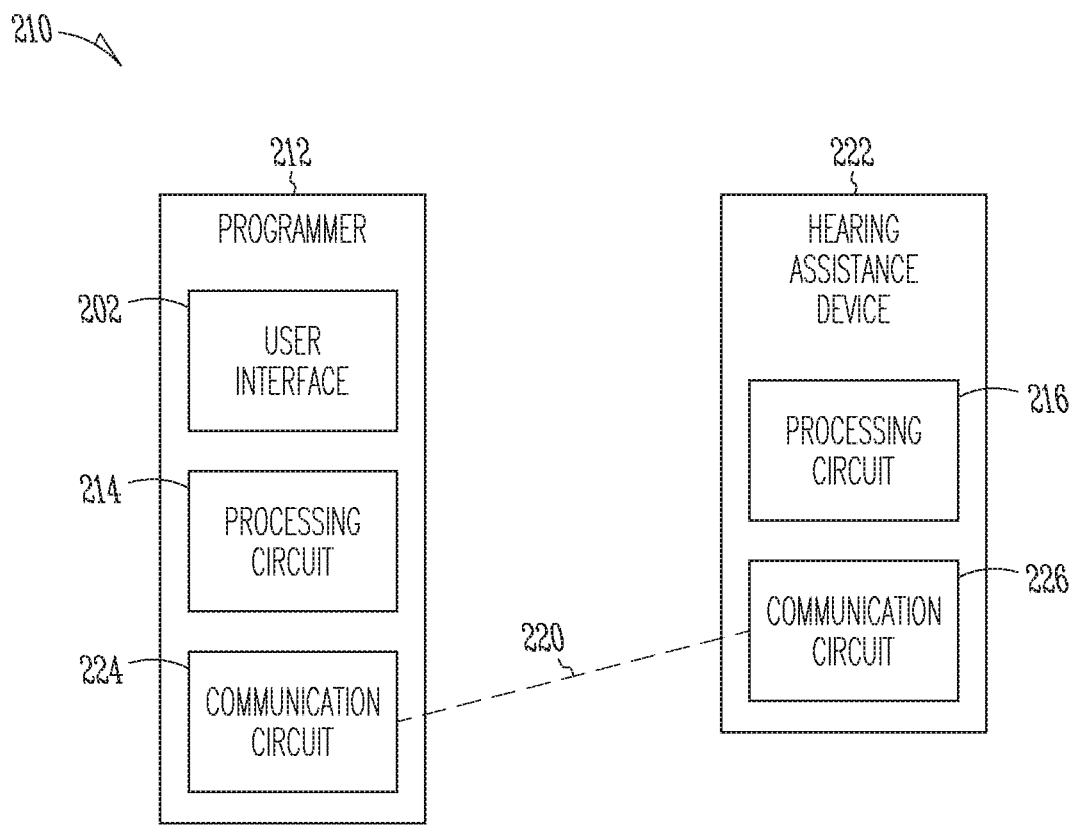
FIG. 2 illustrates a block diagram of a system for programming or fitting a hearing assistance device such as a tinnitus-masker, according to various embodiments of the present subject matter.

FIG. 2 is a block diagram illustrating an embodiment of a hearing assistance system 210 for programming and/or fitting a hearing assistance device, such as a device with a tinnitus-masker. In the illustrated embodiment, system 210 includes a programmer or fitting device 212, a hearing assistance device 222, and a communication link 220 providing for communication between programmer 212 and hearing assistance device 222. In various embodiments, programmer 212 and hearing assistance device 222 may each include one or more devices. For example, programmer 212 may include a computer or a computer connected to a communicator, and hearing assistance device 222 may include a single device or a pair of devices such as a pair of left and right hearing aids or tinnitus-maskers. Communication link 220 may include a wired link or a wireless link. In one embodiment, communication link 220 includes a Bluetooth wireless connection.

Programmer 212 allows for programming of hearing assistance device 222. In various embodiments, programmer 212 may include a computer or other microprocessor-based device programmed to function as a programmer for hearing assistance device 222. Examples of such computer or other microprocessor-based device include a desktop computer, a laptop computer, a tablet computer, a handheld computer, and a cell phone such as a smartphone. Programmer 212 includes a user interface 202, a processing circuit 214, and a communication circuit 224. User interface 202 represents an embodiment of user interface 102. In various embodiments, user interface 202 includes a presentation device including at least a display screen and an input device. In various embodiments, the presentation device may also include various audial and/or visual indicators, and the user input device may include a computer mouse, a touchpad, a trackball, a joystick, a keyboard, and/or a keypad. In one embodiment, user interface 202 includes an interactive screen such as a touchscreen functioning as both the presentation device and the input device. Communication circuit 224 allows signals to be transmitted to and from hearing assistance device 222 via communication link 220. Hearing assistance device 222 includes a processing circuit 216 and a communication circuit 226. Communication circuit 226 allows signals to be transmitted to and from programmer 212 via communication link 220.

In general, previous tinnitus masking stimuli include a broadband noise with a flat spectrum and an overall level set to 10 dB (for closed fits) or 20 dB (for open fits) above the patient's average pure-tone hearing threshold (across 500, 1000, and 4000 Hz) in dB SPL. In addition, the patient can alter the overall level and spectral shape of the stimulus using. One shortcoming of this approach is that there is currently no automated procedure in for checking that the selected tinnitus noise does not interfere substantially with speech intelligibility. In one example, with pure-tone thresholds at 500, 1000, and 4000 Hz in a tinnitus patient are as follows: 25, 35, and 80 dB HL. The average pure-tone threshold across these three frequencies corresponds to approximately 47 dB SPL. Accordingly, the overall level of the tinnitus masker will be set to 57 dB SPL for a closed fit. This corresponds to a per-band level of approximately 45 dB SPL. Even when taking into account the amplification of the speech signal applied by the hearing-aid, the level of the resulting tinnitus masker exceeds the level of a normal conversational speech signal (approximately 65 to 70 dB SPL), especially at low frequencies (below 2-3 kHz), which are critically important for good speech intelligibility.

FIG. 3 illustrates a table showing levels of tinnitus masking and speech at select frequencies, according to various embodiments of the present subject matter. Per-band levels of a 65 dB SPL speech signal (after hearing-aid amplification) and of the tinnitus stimulus in critical bands with center frequencies of 500, 1000, and 2000 Hz, respectively. The levels per band of the normal speech signal are taken from Table 1 of ANSI S3.5-2007. As shown in the present example, the present subject matter verifies that the tinnitus stimulus generated by a hearing aid or some other tinnitus-sound generator does not interfere with speech audibility and intelligibility. The difference in tinnitus stimulus level and normal speech level is shown to increase at increasing frequencies, in various embodiments.

While clinicians can perform such verification themselves, either by performing the same calculations as above or by checking that the patient can still understand speech well when the tinnitus stimulus is playing, and patients may adjust the level of the tinnitus stimulus to avoid speech-understanding difficulties, neither of these two solutions is satisfactory—clinicians have drastic time constraints, and patients cannot be trusted to optimally adjust the volume of their tinnitus sound.

Various embodiments of the present subject matter can be part of a tinnitus-stimulus fitting software. In addition, the present subject matter can be used on its own, or as part of a tinnitus-masker fitting procedure. The present subject matter serves to enhance tinnitus-fitting software and leads to a better solution for the automatic generation of tinnitus stimulus.

Figure 4:
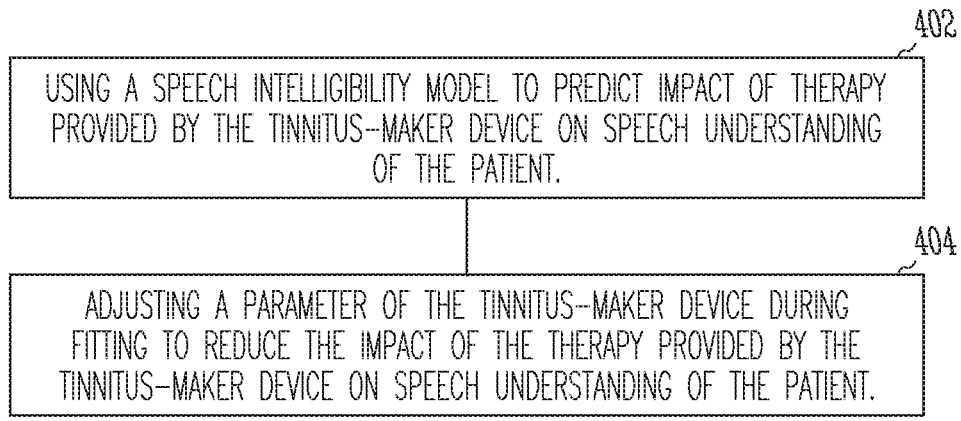
FIG. 4 illustrates a flow diagram of a method for fitting a tinnitus-masker for a patient, according to various embodiments of the present subject matter.

FIG. 4 illustrates a flow diagram of a method for fitting a tinnitus-masker for a patient, according to various embodiments of the present subject matter. The method includes using a speech intelligibility model to predict impact of therapy provided by the tinnitus-maker device on speech understanding of the patient, 402. A parameter of the tinnitus-masker device is adjusted during fitting to reduce the impact of the therapy provided by the tinnitus-maker device on speech understanding of the patient, 404, according to various embodiments. The present subject matter includes a non-transitory computer readable medium to store instructions including the method, and a processor to perform the instructions, in various embodiments.

According to various embodiments, adjusting a parameter of the tinnitus-masker device includes adjusting volume, spectral shape, or modulation rate of an output of the tinnitus-masker device. The method further comprises using the speech intelligibility model to compute adjustments of the parameters of the tinnitus-masker device during fitting, in various embodiments. In one embodiment, using a speech intelligibility model to predict impact of therapy provided by the tinnitus-maker device on speech understanding of the patient includes using a proficiency factor incorporating a relationship between computed audibility of speech signals and predicted speech intelligibility. Various embodiments include estimating audibility of conversational speech in different frequency bands. The method includes using the estimated audibility of conversational speech to compute speech intelligibility scores with and without the therapy provided by the tinnitus-masker device, in an embodiment. In various embodiments, the present description relates to computing a corrected speech intelligibility score using a measured or estimated proficiency factor of the patient. The method includes comparing the corrected speech intelligibility score to a predefined threshold, and providing an option to a user to adjust the parameter of the tinnitus-masker device if the threshold is exceeded, in an embodiment.

Figure 5:
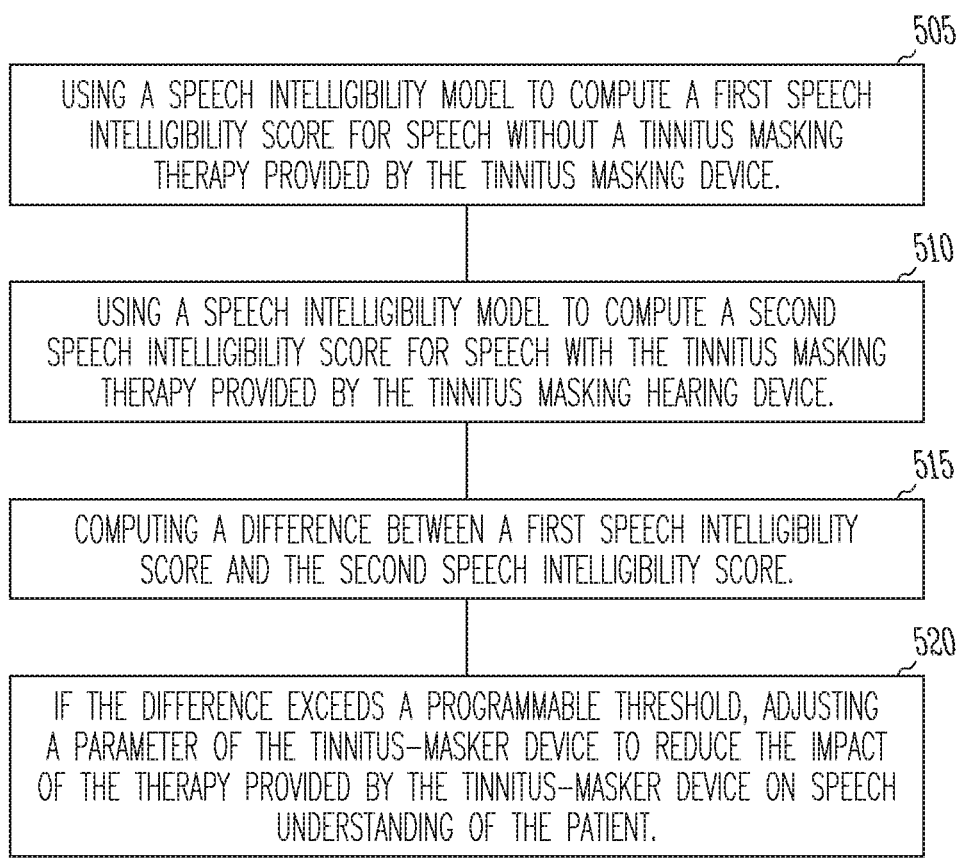
FIG. 5 illustrates a flow diagram of a method for automated assessment and adjustment of tinnitus-masker impact on speech intelligibility during fitting, according to various embodiments of the present subject matter.

FIG. 5 illustrates a flow diagram of a method for automated assessment and adjustment of tinnitus-masker impact on speech intelligibility during fitting, according to various embodiments of the present subject matter. A speech intelligibility model is used to compute a first speech intelligibility score for speech without a tinnitus masking therapy provided by the tinnitus masking hearing device, 505. The speech intelligibility model is used to compute a second speech intelligibility score for speech with the tinnitus masking therapy provided by the tinnitus masking hearing device, 510. A difference is computed between the first speech intelligibility score and the second speech intelligibility score, 515. If the difference exceeds a programmable threshold, a parameter of the tinnitus-masker device is adjusted to reduce the impact of the therapy provided by the tinnitus-maker device on speech understanding of the patient, 520, in various embodiments. The present subject matter includes a non-transitory computer readable medium to store instructions including the method, and a processor to perform the instructions, in various embodiments.

According to various embodiments, adjusting a parameter of the tinnitus-masker device includes providing an option to a user of the fitting device to adjust the parameter of the tinnitus-masker device. Adjusting a parameter of the tinnitus-masker device includes automatically adjusting the parameter of the tinnitus-masker device, in various embodiments. The method includes using an audiogram of the patient to compute at least one of the first and second speech intelligibility score, in an embodiment. In one embodiment, the first and second speech intelligibility scores are computed at approximately 65 to 70 dB for normal conversational speech level. Adjusting a parameter of the tinnitus-masker device includes adjusting volume, spectral shape and/or modulation rate of an output of the tinnitus-masker device, in various embodiments.

Adjustment During Use

The present subject matter includes automated assessment and adjustment of tinnitus-masker impact on speech intelligibility during use of the hearing device. In the present subject matter, the speech-model-based algorithm is combined with a computational scene-analysis algorithm, and potentially other measures (e.g., measures of brain activity) to allow for automatic readjustment of the masker volume and spectral characteristics of the therapeutic sound (TS) whenever needed while the user is wearing the device.

The above method is aimed at facilitating the selection or the adjustment by the clinician, at the time of fitting, of the overall volume and/or spectrum of the TS, while controlling for expected masking of speech by the TS, on average (based on expected, long-term average speech levels). However, the level of speech in the listener's environment can fluctuate over time, depending on factors such as the distance and vocal effort of the talker. In addition, in some cases (e.g., patients with highly elevated hearing thresholds in frequency regions that contain important speech information) the highest volume of the TS that does not interfere with the perception of speech at a conversational level, is lower than the level needed for the TS to have its expected effect on tinnitus (e.g., masking). In such cases, it is impossible to fix the volume of the TS in such a way that it acts as intended, while not interfering with speech.

The present subject matter addresses these limitations by using an algorithm embedded on the device (hearing aid or other TS-generating device) to automatically readjust the volume and/or spectrum of the TS over time, depending on current listening conditions. The adaptation to current conditions is achieved using automatic analysis of the listener's acoustic environment (e.g., is there a speech signal in the environment?) as well as, potentially, information concerning the listener's current intentions (e.g., is the listener currently trying to listen to the speech signal?).

According to various embodiments, the present subject matter monitors sound incoming into a device to decide whether speech is present, and whether external noise is present. If speech is detected, the device estimates the level of the speech signal and possibly other measures, such as modulation characteristics, which can be used to estimate whether the speech signal is accompanied by other signals or noise, what the signal-to-noise ratio of the speech signal is, as well as other acoustic or psychoacoustic variables that can be used advantageously in subsequent adjustment of the TS. The present subject matter uses a model of speech intelligibility to estimate the impact of the TS on the perception of the speech signal by the user, and the estimated impact is used, if necessary, to readjust the level and/or spectrum of the TS, so as to reduce the impact to a predefined acceptable level.

In an alternate embodiment, the present subject matter additionally measures, or estimates, the listener's intent (e.g., using body or brain signals to infer whether the listener is listening to one of speech signals in the environment or not). This additional information is then used to modulate the adjustment of the TS level or spectrum (e.g., if the listener is not trying to listen to speech signals around him/her, then there may not be a need to lower the volume of the TS).

Figure 6:
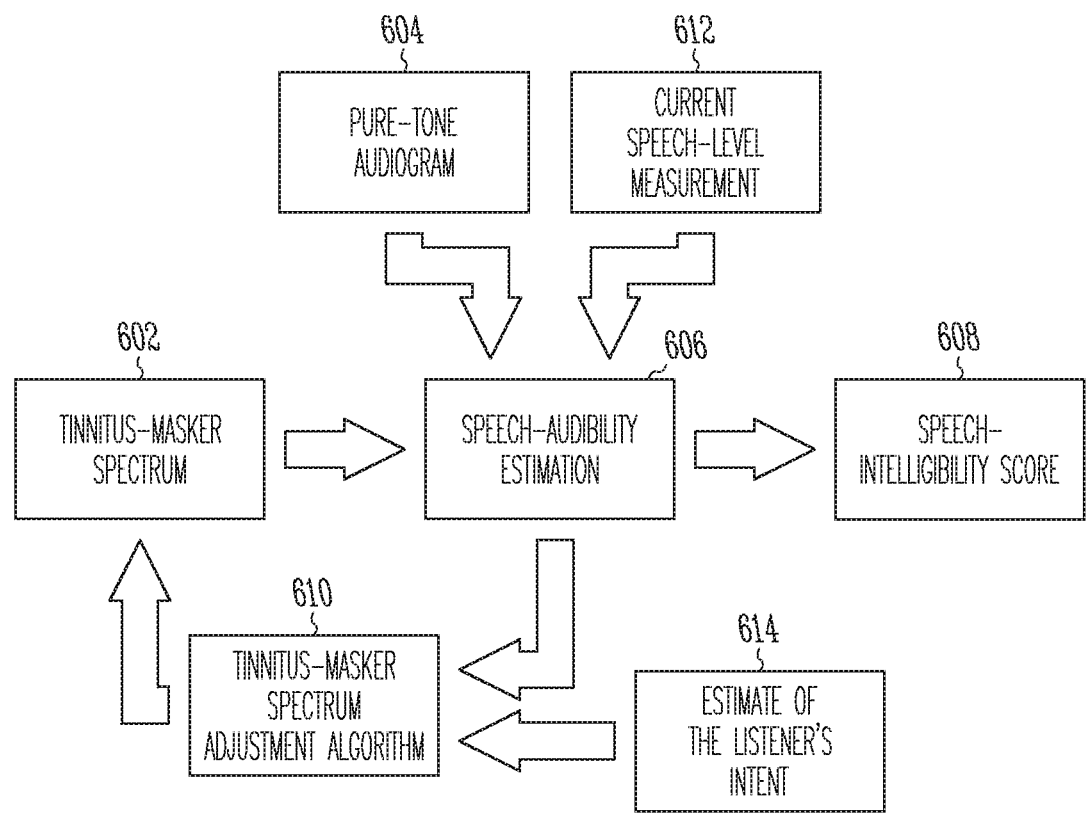
FIG. 6 illustrates a block diagram of system for limiting tinnitus-masker impact on speech intelligibility during use of the tinnitus-masker, according to various embodiments of the present subject matter.

FIG. 6 illustrates a block diagram of system for limiting tinnitus-masker impact on speech intelligibility during use of the tinnitus-masker, according to various embodiments of the present subject matter.

The current, or 'reference', spectrum 602 of the TS is used as input, along with the patient's audiogram 604 and a measure 612 of the current level of speech in the environment (which may equal a very low value when no speech is detected), to a speech-audibility estimation model 606. Based on the results, speech-intelligibility scores 608 are computed with, and without, the tinnitus masker, using a speech-intelligibility model. If the speech-intelligibility score 608 (or the speech audibility) with the masker is too low, taking into account the speech-intelligibility score without the masker, the overall volume and spectrum 610 of the TS is readjusted to limit its impact on speech intelligibility to a predefined acceptable level.

The mathematical description of the present subject matter is closely aligned with the fitting embodiment. The main difference is that, in the initial step in the companion invention, the computation of the audibility of the speech signal, A[f], is based, not on the assumed normal conversational level of speech (65 dB SPL), but on the current level of speech, measured using the device.

In an alternate embodiment of the present subject matter, body or brain signals (e.g., EEG signals) are additionally used to make an inference concerning the listener's intent 614, e.g., his/her attentional goals. For instance, if speech has been detected in the listener's environment, but the listener is not currently listening to the speech (which can, in theory, be inferred using EEG signals from the listener's brain or from his/her eye movements, as may be the case if the listener is currently reading), the adjustment of the overall volume and/or spectrum of the masker may be deferred.

While the above embodiment was limited to the time of fitting of the device (hearing-aid or other), using an algorithm inside the fitting software, the present subject matter is intended to run constantly, or periodically, on the device, so that it can reside on hardware (integrated circuit) or firmware (algorithm running on the device). In the fitting embodiment, the computation of the speech-masking effect of the TS was performed with respect to a fixed and assumed, long-term average speech level (e.g., 65 dB SPL). In the present embodiment, the presence and level of speech is actually measured (or estimated) in the listener's environment, while the listener is using the device, and the level and/or spectrum of the TS is readjusted, whenever necessary, from moment to moment. According to various embodiments, this subject matter is as part of a hearing assistance device, which also generates a TS for tinnitus. Alternatively, the present subject matter can be put on a tinnitus-masking device that is not a hearing aid.

Figure 7:
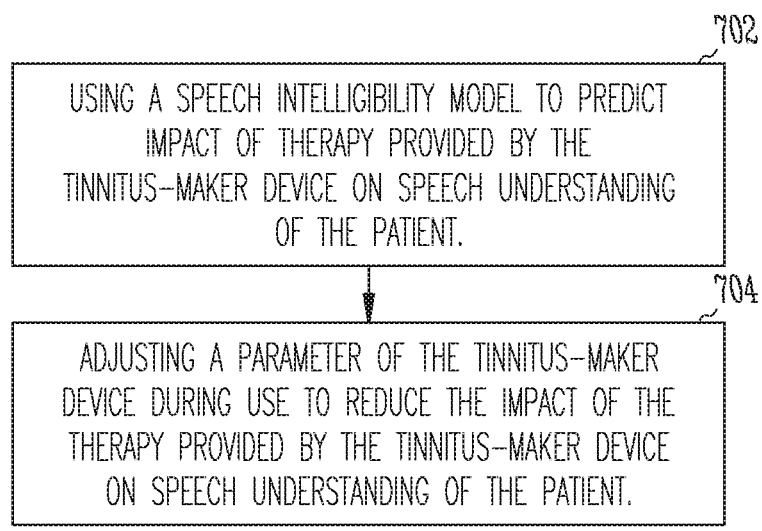
FIG. 7 illustrates a flow diagram of a method for automated assessment and adjustment of tinnitus-masker impact on speech intelligibility during use, according to various embodiments of the present subject matter.

FIG. 7 illustrates a flow diagram of a method for automated assessment and adjustment of tinnitus-masker impact on speech intelligibility during use, according to various embodiments of the present subject matter. The method includes using a speech intelligibility model to predict impact of therapy provided by the tinnitus-maker device on speech understanding of the patient 702, and automatically adjusting a parameter of the tinnitus-masker device during use of the device to reduce the impact of the therapy provided by the tinnitus-maker device on speech understanding of the patient 704.

Hearing assistance devices typically include at least one enclosure or housing, a microphone, hearing assistance device electronics including processing electronics, and a speaker or "receiver." Hearing assistance devices can include a power source, such as a battery. In various embodiments, the battery is rechargeable. In various embodiments multiple energy sources are employed. It is understood that in various embodiments the microphone is optional. It is understood that in various embodiments the receiver is optional. It is understood that variations in communications protocols, antenna configurations, and combinations of components can be employed without departing from the scope of the present subject matter. Antenna configurations can vary and can be included within an enclosure for the electronics or be external to an enclosure for the electronics. Thus, the examples set forth herein are intended to be demonstrative and not a limiting or exhaustive depiction of variations.

It is understood that digital hearing assistance devices include a processor. In digital hearing assistance devices with a processor, programmable gains can be employed to adjust the hearing assistance device output to a wearer's particular hearing impairment. The processor can be a digital signal processor (DSP), microprocessor, microcontroller, other digital logic, or combinations thereof. The processing can be done by a single processor, or can be distributed over different devices. The processing of signals referenced in this application can be performed using the processor or over different devices. Processing can be done in the digital domain, the analog domain, or combinations thereof. Processing can be done using subband processing techniques. Processing can be done using frequency domain or time domain approaches. Some processing can involve both frequency and time domain aspects. For brevity, in some examples drawings can omit certain blocks that perform frequency synthesis, frequency analysis, analog-to-digital conversion, digital-to-analog conversion, amplification, buffering, and certain types of filtering and processing. In various embodiments of the present subject matter the processor is adapted to perform instructions stored in one or more memories, which can or cannot be explicitly shown. Various types of memory can be used, including volatile and nonvolatile forms of memory. In various embodiments, the processor or other processing devices execute instructions to perform a number of signal processing tasks. Such embodiments can include analog components in communication with the processor to perform signal processing tasks, such as sound reception by a microphone, or playing of sound using a receiver (i.e., in applications where such transducers are used). In various embodiments of the present subject matter, different realizations of the block diagrams, circuits, and processes set forth herein can be created by one of skill in the art without departing from the scope of the present subject matter.

It is further understood that different hearing assistance devices can embody the present subject matter without departing from the scope of the present disclosure. The devices depicted in the figures are intended to demonstrate the subject matter, but not necessarily in a limited, exhaustive, or exclusive sense. It is also understood that the present subject matter can be used with a device designed for use in the right ear or the left ear or both ears of the wearer.

The present subject matter is demonstrated for hearing assistance devices, including hearing assistance devices, including but not limited to, behind-the-ear (BTE), in-the-ear (ITE), in-the-canal (ITC), receiver-in-canal (RIC), invisible-in-canal (IIC) or completely-in-the-canal (CIC) type hearing assistance devices. It is understood that behind-the-ear type hearing assistance devices can include devices that reside substantially behind the ear or over the ear. Such devices can include hearing assistance devices with receivers associated with the electronics portion of the behind-the-ear device, or hearing assistance devices of the type having receivers in the ear canal of the user, including but not limited to receiver-in-canal (RIC) or receiver-in-the-ear (RITE) designs. The present subject matter can also be used in hearing assistance devices generally, such as cochlear implant type hearing devices. The present subject matter can also be used in deep insertion devices having a transducer, such as a receiver or microphone. The present subject matter can be used in devices whether such devices are standard or custom fit and whether they provide an open or an occlusive design. It is understood that other hearing assistance devices not expressly stated herein can be used in conjunction with the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A method of using a tinnitus-masker device for a patient, the method comprising:
   using a speech intelligibility model to compute a first speech intelligibility score without a tinnitus-masking therapy provided by the device and a second speech intelligibility score with the tinnitus masking therapy;
   computing a difference between the first and second speech intelligibility scores; and
   if the difference exceeds a programmable threshold, automatically adjusting a parameter of the tinnitus-masker device during use of the device to reduce the impact of the therapy provided by the tinnitus-masker device on speech understanding of the patient.

2. The method of claim 1, wherein adjusting a parameter of the tinnitus-masker device includes adjusting volume, spectral shape, or modulation rate of an output of the tinnitus-masker device.

3. The method of claim 1, comprising using the speech intelligibility model to compute adjustments of the parameters of the tinnitus-masker device during use.

4. The method of claim 1, wherein using a speech intelligibility model to predict impact of therapy provided by the tinnitus-masker device on speech understanding of the patient includes using a proficiency factor incorporating a relationship between computed audibility of speech signals and predicted speech intelligibility.

5. The method of claim 1, wherein using a speech intelligibility model to predict impact of therapy provided by the tinnitus-masker device on speech understanding of the patient includes estimating audibility of conversational speech in different frequency bands.

6. The method of claim 5, comprising using the estimated audibility of conversational speech to compute speech intelligibility scores with and without the therapy provided by the tinnitus-masker device.

7. The method of claim 1, comprising computing a corrected speech intelligibility score using a measured or estimated proficiency factor of the patient.

8. The method of claim 7, comprising comparing the corrected speech intelligibility score to a predefined threshold, and providing an option to a user to adjust the parameter of the tinnitus-masker device if the threshold is exceeded.

9. A tinnitus masking hearing device for a patient, the device comprising:
   a sound generator configured to provide tinnitus masking therapy; and
   a processor connected to the sound generator, the processor programmed with instructions to perform:
   using a speech intelligibility model to compute a first speech intelligibility score for speech without a tinnitus masking therapy provided by the tinnitus masking hearing device;
   using the speech intelligibility model to compute a second speech intelligibility score for speech with the tinnitus masking therapy provided by the tinnitus masking hearing device;
   computing a difference between the first speech intelligibility score and the second speech intelligibility score; and
   if the difference exceeds a programmable threshold, adjusting a parameter of the tinnitus-masker device to reduce the impact of the therapy provided by the tinnitus-masker device on speech understanding of the patient.

10. The device of claim 9, wherein adjusting a parameter of the tinnitus-masker device includes providing an option to a user of the device to adjust the parameter of the tinnitus-masker device.

11. The fitting device of claim 9, wherein adjusting a parameter of the tinnitus-masker device includes automatically adjusting the parameter of the tinnitus-masker device.

12. The fitting device of claim 9, wherein the processor is further configured with instructions to perform:
   using an audiogram of the patient to compute at least one of the first and second speech intelligibility score.

13. The fitting device of claim 9, wherein the first and second speech intelligibility scores are computed at approximately 65 to 70 dB for normal conversational speech level.

14. The fitting device of claim 9, wherein adjusting a parameter of the tinnitus-masker device includes adjusting volume of an output of the tinnitus-masker device.

15. The fitting device of claim 9, wherein adjusting a parameter of the tinnitus-masker device includes adjusting spectral shape of an output of the tinnitus-masker device.

16. The fitting device of claim 9, wherein adjusting a parameter of the tinnitus-masker device includes adjusting modulation rate of an output of the tinnitus-masker device.

17. A non-transitory computer-readable storage medium that stores instructions for execution by processing circuitry of a tinnitus masking hearing device for a patient, the operations including:
   using a speech intelligibility model to compute a first speech intelligibility score for speech without a tinnitus masking therapy provided by the tinnitus masking hearing device;
   using the speech intelligibility model to compute a second speech intelligibility score for speech with the tinnitus masking therapy provided by the tinnitus masking hearing device;
   computing a difference between the first speech intelligibility score and the second speech intelligibility score; and
   if the difference exceeds a programmable threshold, adjusting a parameter of the tinnitus-masker device to reduce the impact of the therapy provided by the tinnitus-masker device on speech understanding of the patient.

18. The computer-readable storage medium of claim 17, wherein adjusting a parameter of the tinnitus-masker device includes adjusting volume of an output of the tinnitus-masker device.

19. The computer-readable storage medium of claim 17, wherein adjusting a parameter of the tinnitus-masker device includes adjusting spectral shape of an output of the tinnitus-masker device.

20. The computer-readable storage medium of claim 17, wherein adjusting a parameter of the tinnitus-masker device includes adjusting modulation rate of an output of the tinnitus-masker device.

* * * * *